US011646341B2

(12) United States Patent
Zaizen et al.

(10) Patent No.: US 11,646,341 B2
(45) Date of Patent: May 9, 2023

(54) LIGHT-RECEIVING DEVICE, METHOD OF MANUFACTURING LIGHT-RECEIVING DEVICE, AND ELECTRONIC APPARATUS

(71) Applicant: SONY SEMICONDUCTOR SOLUTIONS CORPORATION, Kanagawa (JP)

(72) Inventors: Yoshifumi Zaizen, Kanagawa (JP); Shunsuke Maruyama, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

(21) Appl. No.: 16/340,305

(22) PCT Filed: Oct. 6, 2017

(86) PCT No.: PCT/JP2017/036431
§ 371 (c)(1),
(2) Date: Apr. 8, 2019

(87) PCT Pub. No.: WO2018/088083
PCT Pub. Date: May 17, 2018

(65) Prior Publication Data
US 2019/0319055 A1    Oct. 17, 2019

(30) Foreign Application Priority Data
Nov. 11, 2016   (JP) .............................. JP2016-220762

(51) Int. Cl.
*H01L 27/146*   (2006.01)
*H01L 31/0304*  (2006.01)
(Continued)

(52) U.S. Cl.
CPC ...... *H01L 27/1465* (2013.01); *H01L 27/1463* (2013.01); *H01L 27/14636* (2013.01);
(Continued)

(58) Field of Classification Search
CPC .......... H01L 27/1465; H01L 27/14694; H01L 31/03046; H01L 31/1844; H01L 27/1463;
(Continued)

(56) References Cited

U.S. PATENT DOCUMENTS

2005/0035381 A1*   2/2005   Holm .................. H01L 27/1463
                                                             257/290
2007/0264835 A1    11/2007  Iguchi et al.
(Continued)

FOREIGN PATENT DOCUMENTS

JP    63-160283 A     7/1988
JP    2007-324572 A   12/2007
(Continued)

OTHER PUBLICATIONS

International Search Report and Written Opinion of PCT Application No. PCT/JP2017/036431, dated Nov. 7, 2017, 09 pages of ISRWO.

*Primary Examiner* — Monica D Harrison
*Assistant Examiner* — John Lin
(74) *Attorney, Agent, or Firm* — Chip Law Group

(57) ABSTRACT

A light-receiving device of an embodiment of the present disclosure includes a photoelectric conversion layer that includes a first compound semiconductor with a first conductivity type and absorbs a wavelength of an infrared region, a first semiconductor layer formed on the photoelectric conversion layer, and an insulation layer formed to surround the photoelectric conversion layer and the first semiconductor layer, the first semiconductor layer having a second conductivity-type region at a middle region excluding a periphery facing the photoelectric conversion layer.

13 Claims, 12 Drawing Sheets

(51) Int. Cl.
*H01L 31/109* (2006.01)
*H01L 31/18* (2006.01)
*A61B 1/04* (2006.01)
*B60W 50/00* (2006.01)
*H04N 5/33* (2023.01)

(52) U.S. Cl.
CPC .. *H01L 27/14694* (2013.01); *H01L 31/03046* (2013.01); *H01L 31/109* (2013.01); *H01L 31/1844* (2013.01); *A61B 1/041* (2013.01); *B60W 50/00* (2013.01); *H01L 27/14621* (2013.01); *H01L 27/14627* (2013.01); *H04N 5/33* (2013.01)

(58) Field of Classification Search
CPC ............ H01L 31/109; H01L 27/14636; H01L 27/14669; H01L 27/14603; H01L 27/14605; A61B 1/041
See application file for complete search history.

(56) References Cited

U.S. PATENT DOCUMENTS

| | | | | |
|---|---|---|---|---|
| 2010/0044677 | A1* | 2/2010 | Nagai | B82Y 20/00 257/21 |
| 2014/0217543 | A1* | 8/2014 | Ni | H01L 27/1465 257/448 |
| 2014/0225063 | A1* | 8/2014 | Klem | H01L 51/0046 257/14 |

FOREIGN PATENT DOCUMENTS

| | | |
|---|---|---|
| JP | 2009-105105 A | 5/2009 |
| JP | 2010-205858 A | 9/2010 |
| JP | 2011-192838 A | 9/2011 |

\* cited by examiner

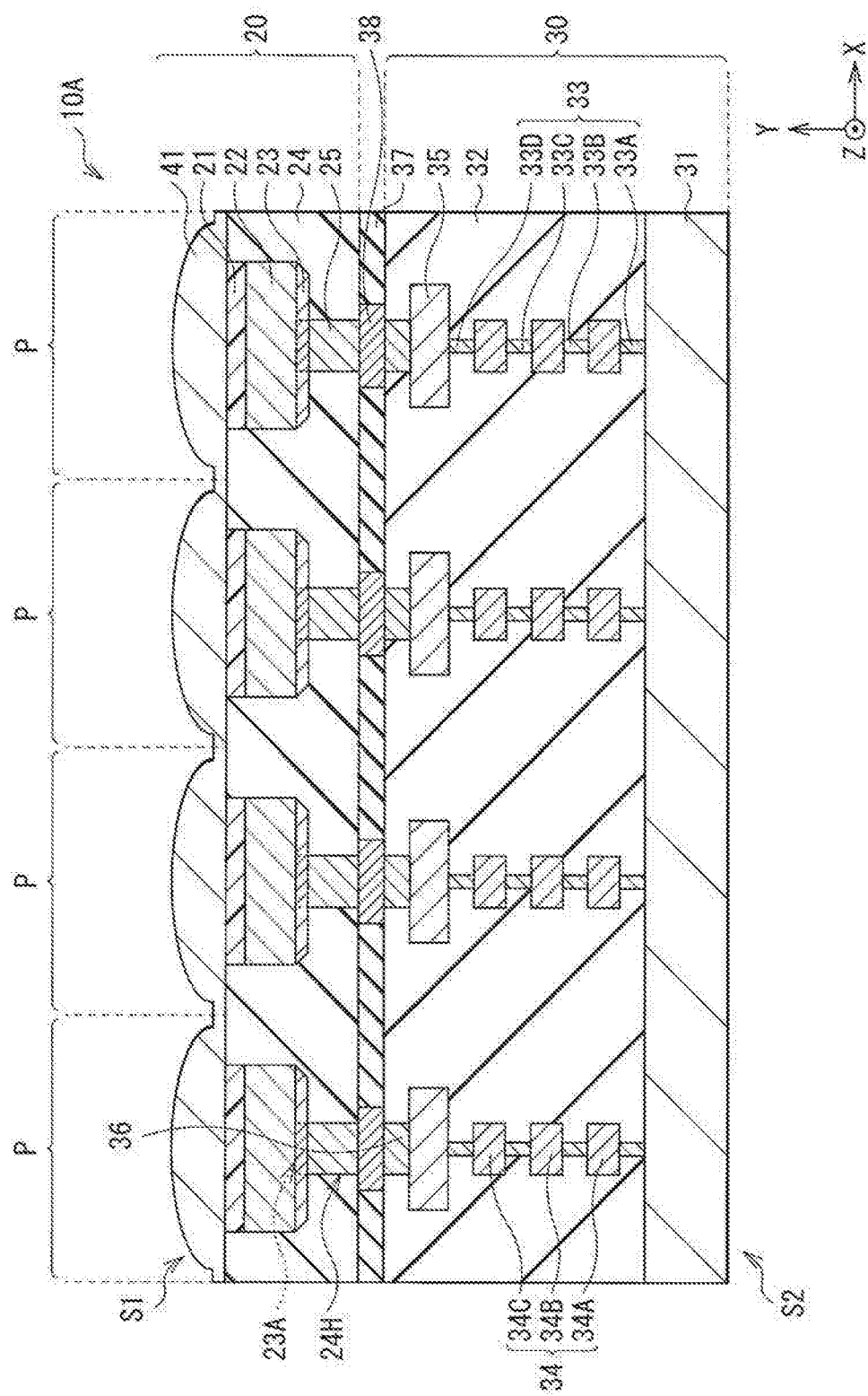
[FIG. 1]

[FIG. 2A]
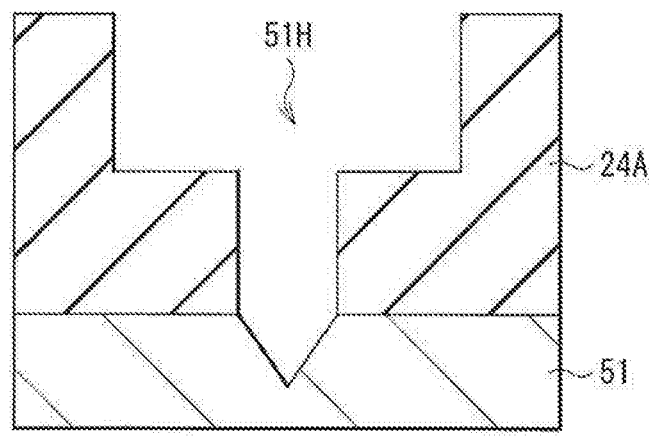
[FIG. 2B]
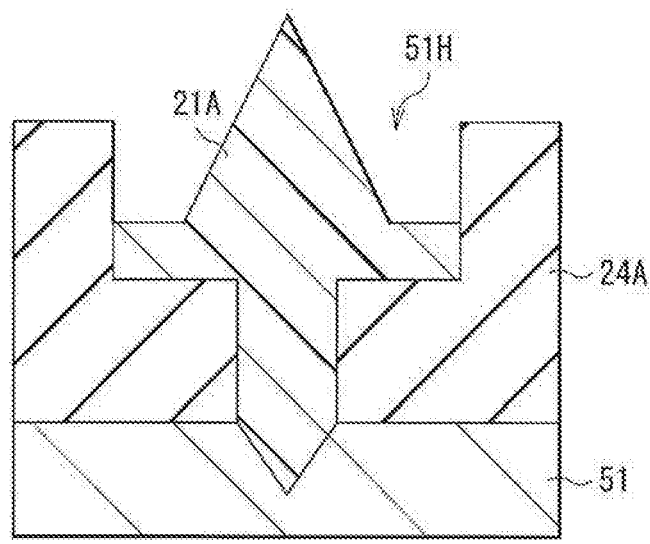
[FIG. 2C]
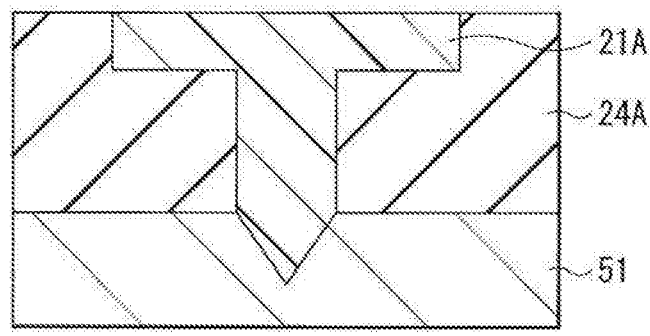

[FIG. 3A]
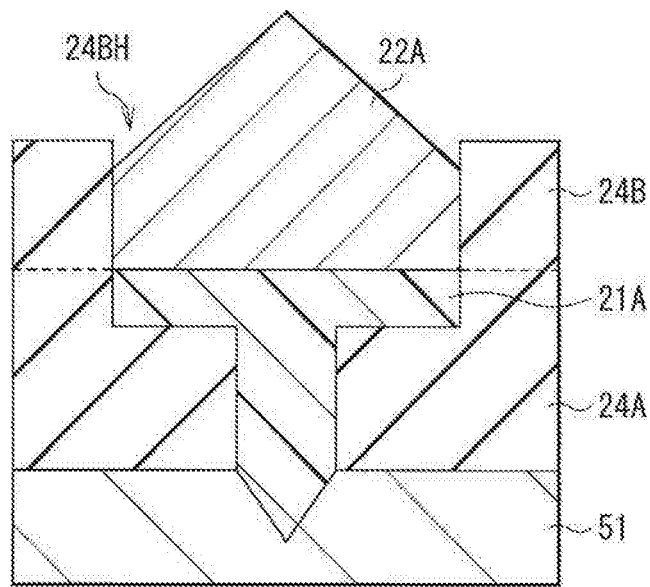
[FIG. 3B]
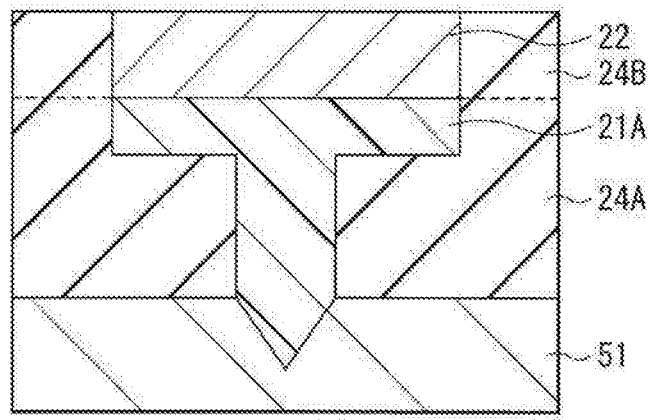
[FIG. 3C]
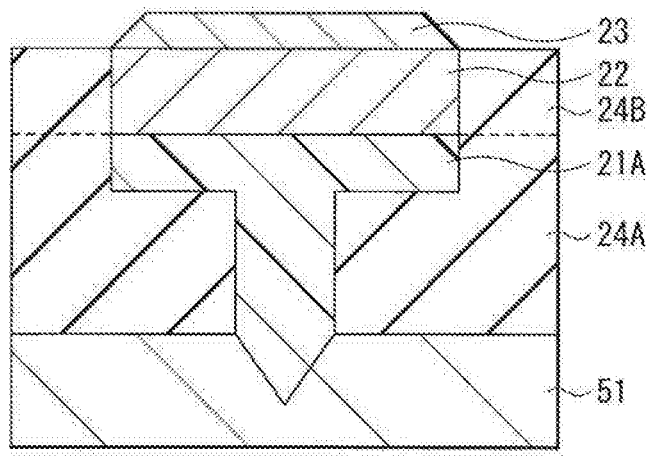

[ FIG. 4A ]
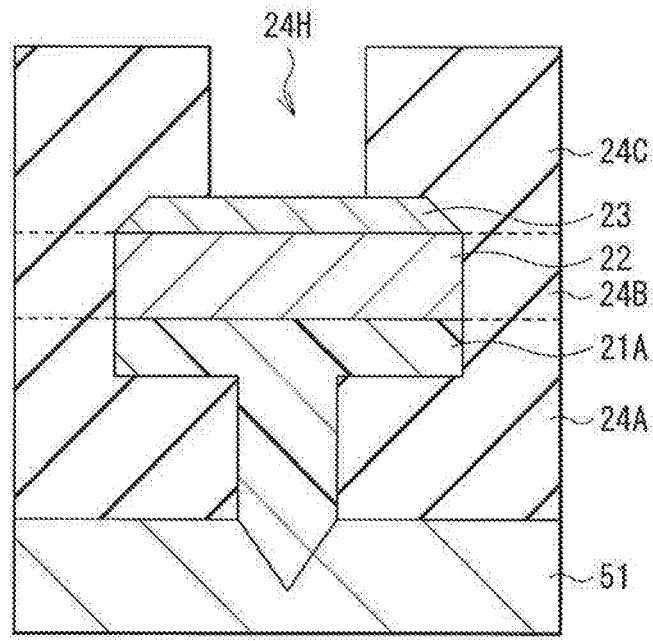
[ FIG. 4B ]
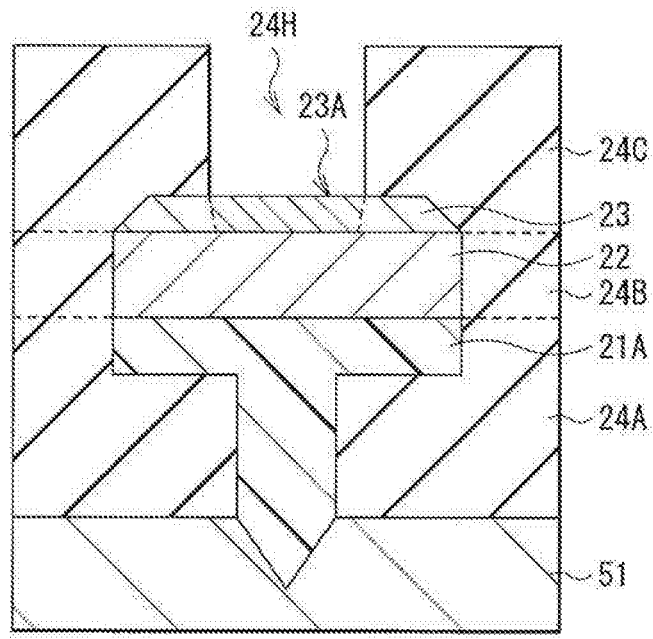

[FIG. 5A]
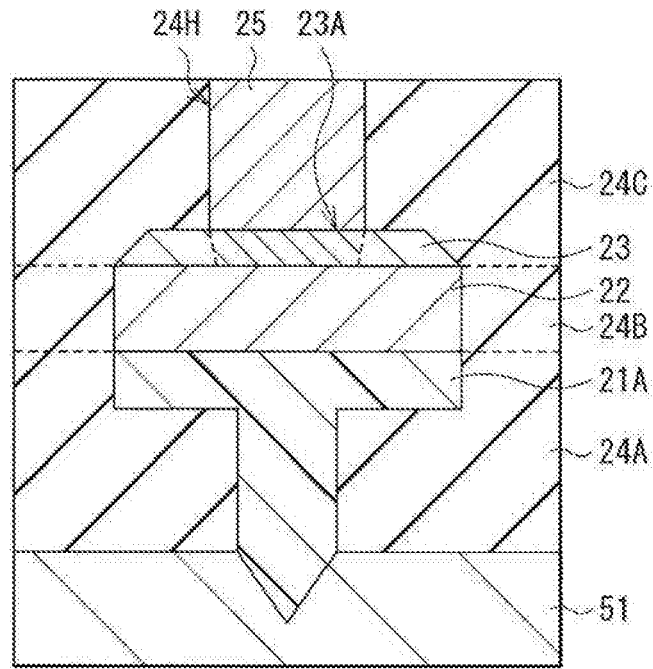
[FIG. 5B]
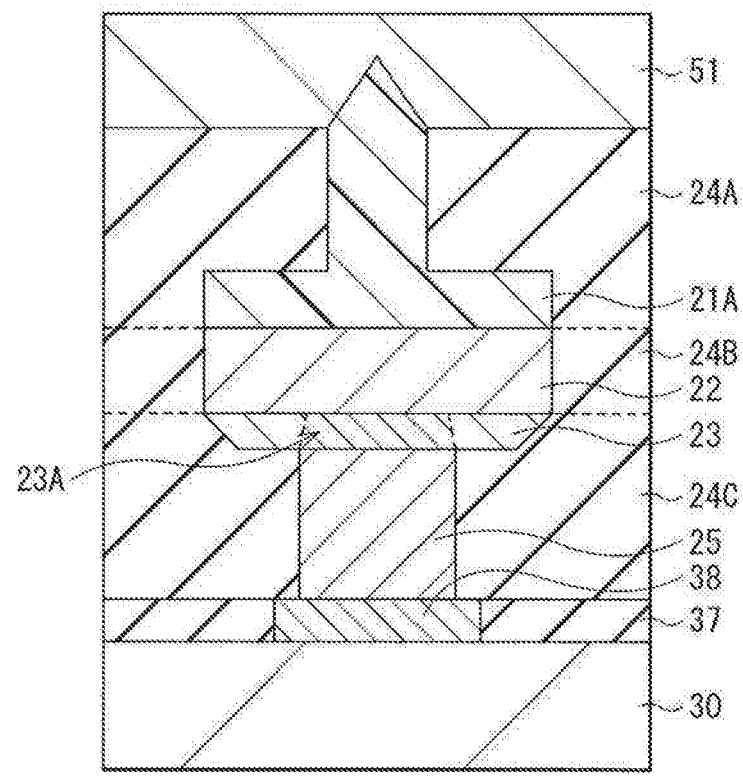

[FIG. 6]
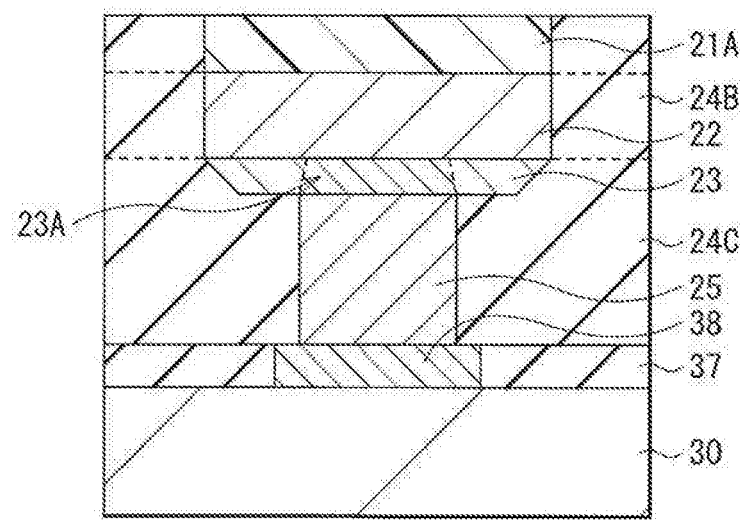

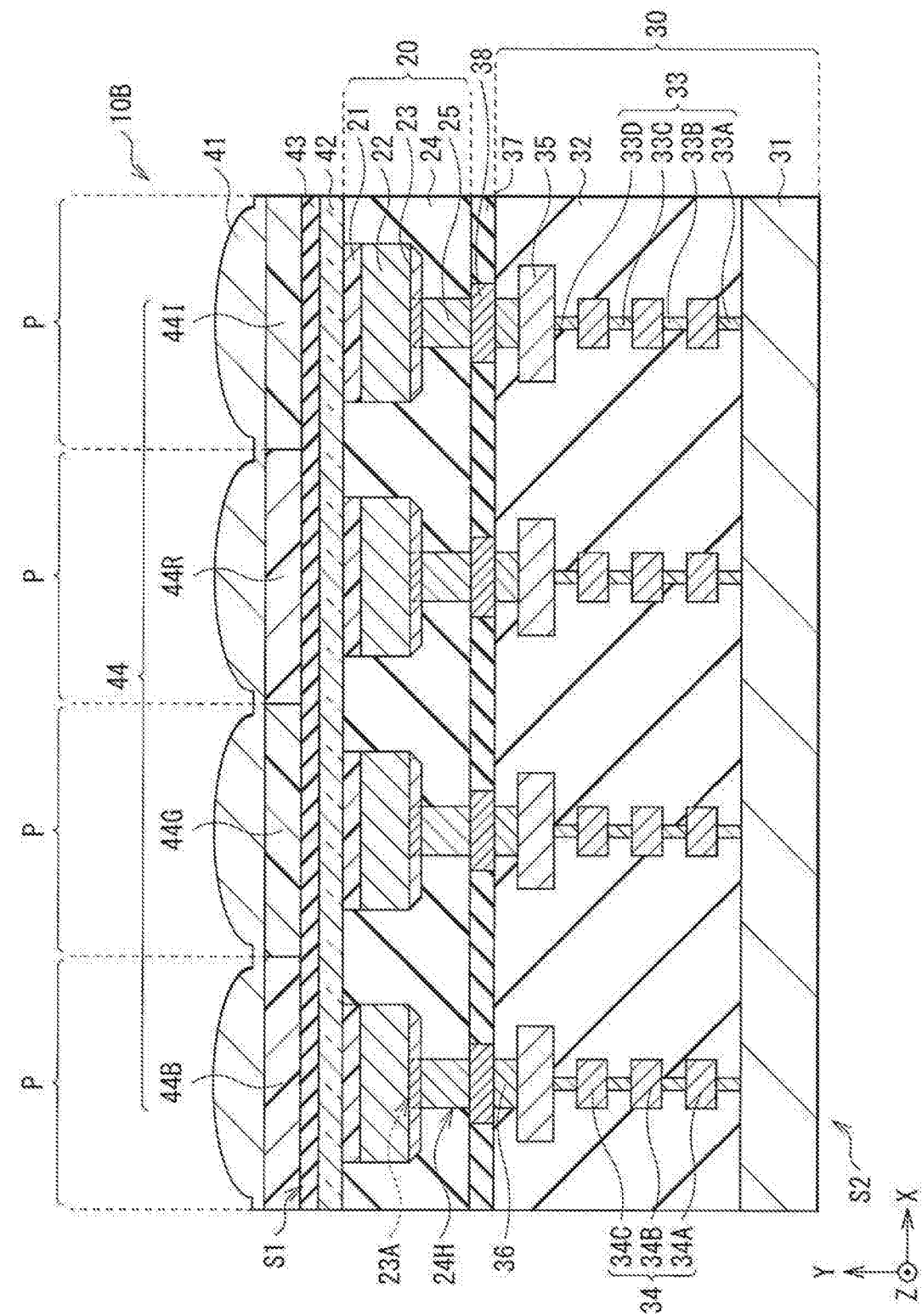
[FIG. 7]

[FIG. 8]
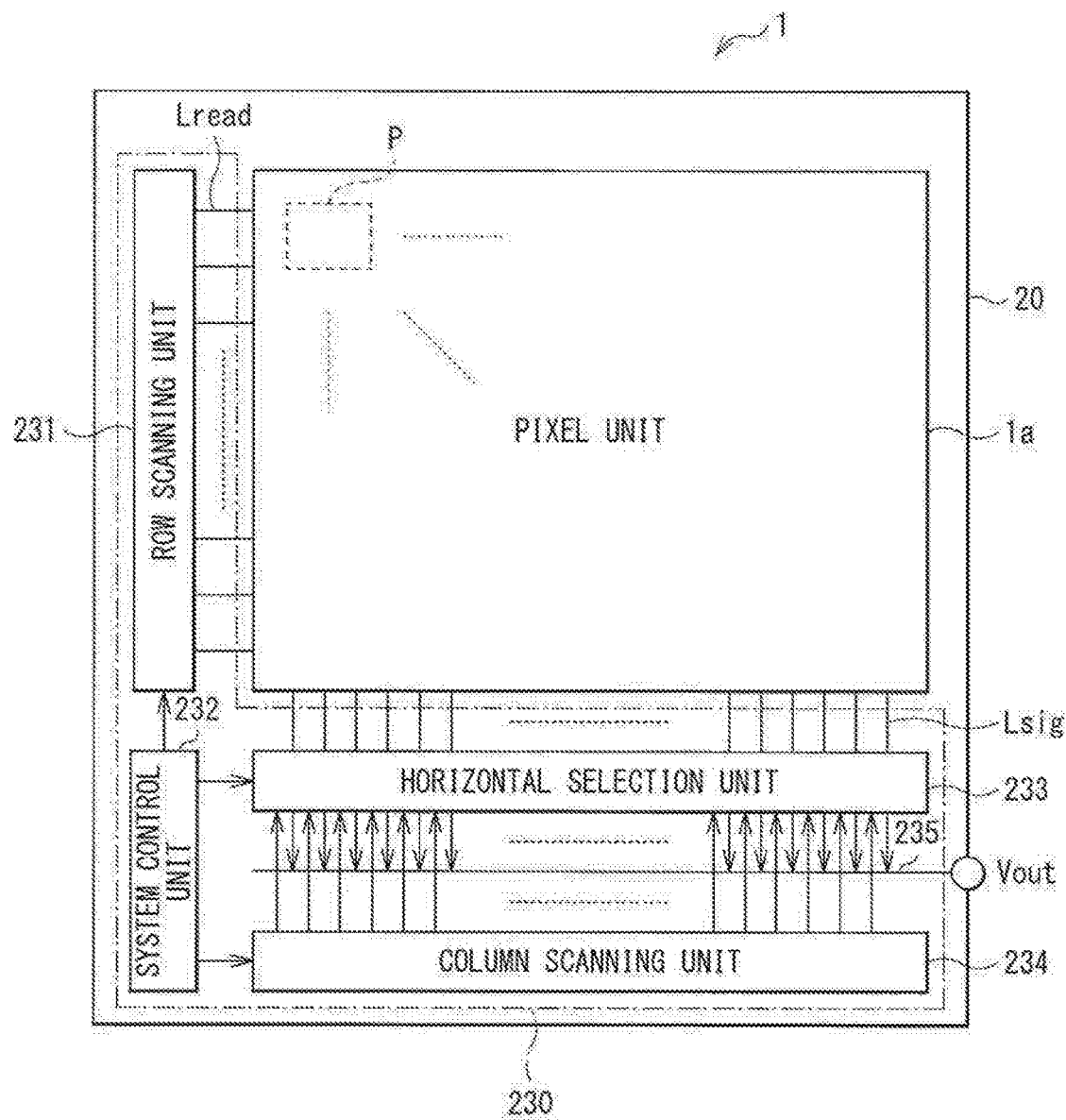

[FIG. 9]
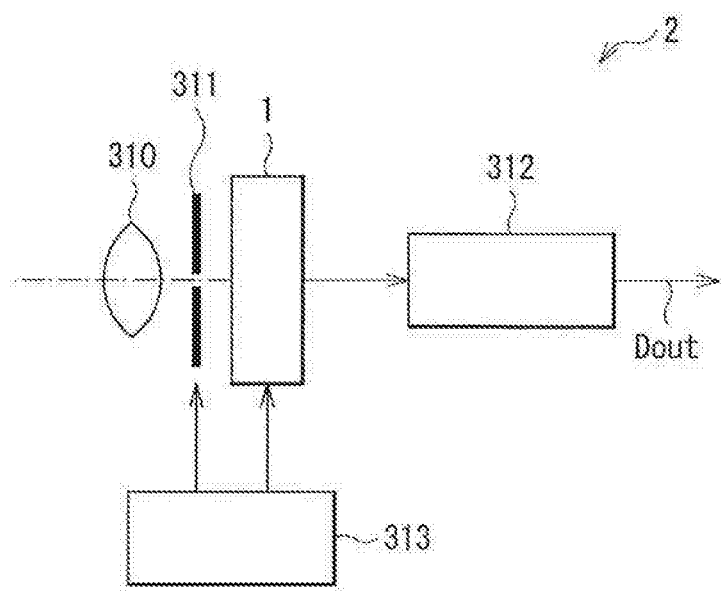

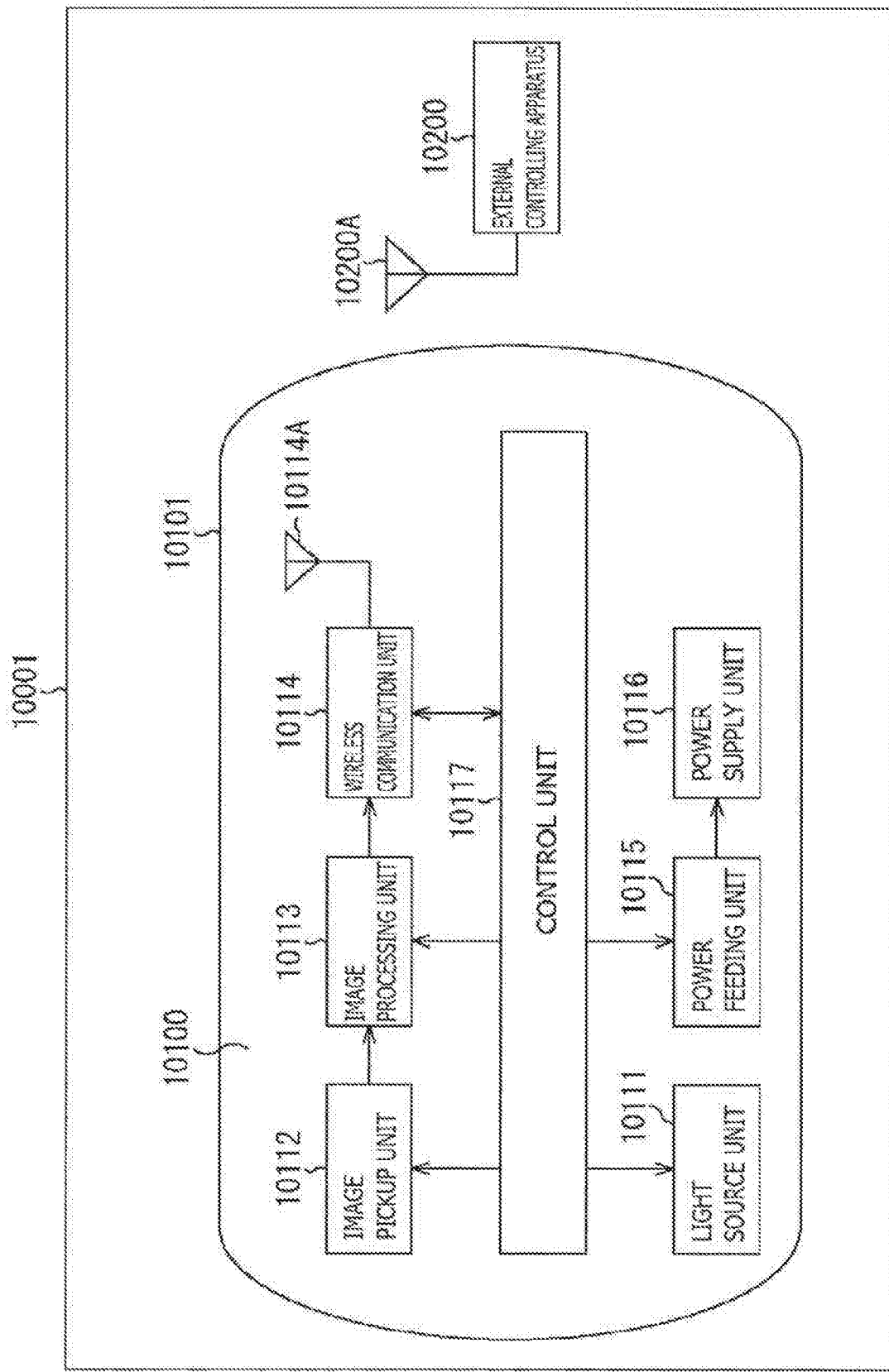

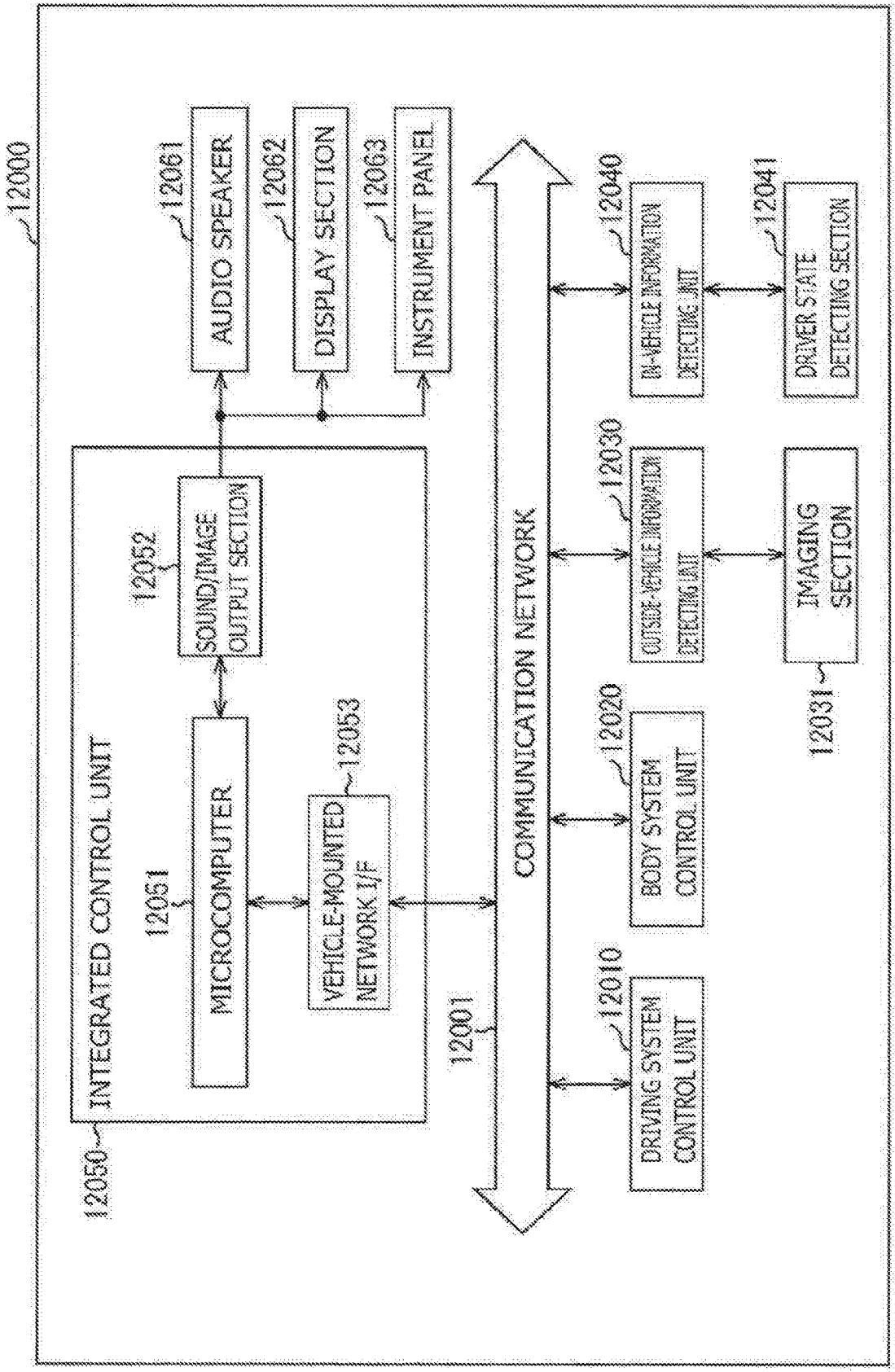
[FIG. 11]

[FIG. 12]
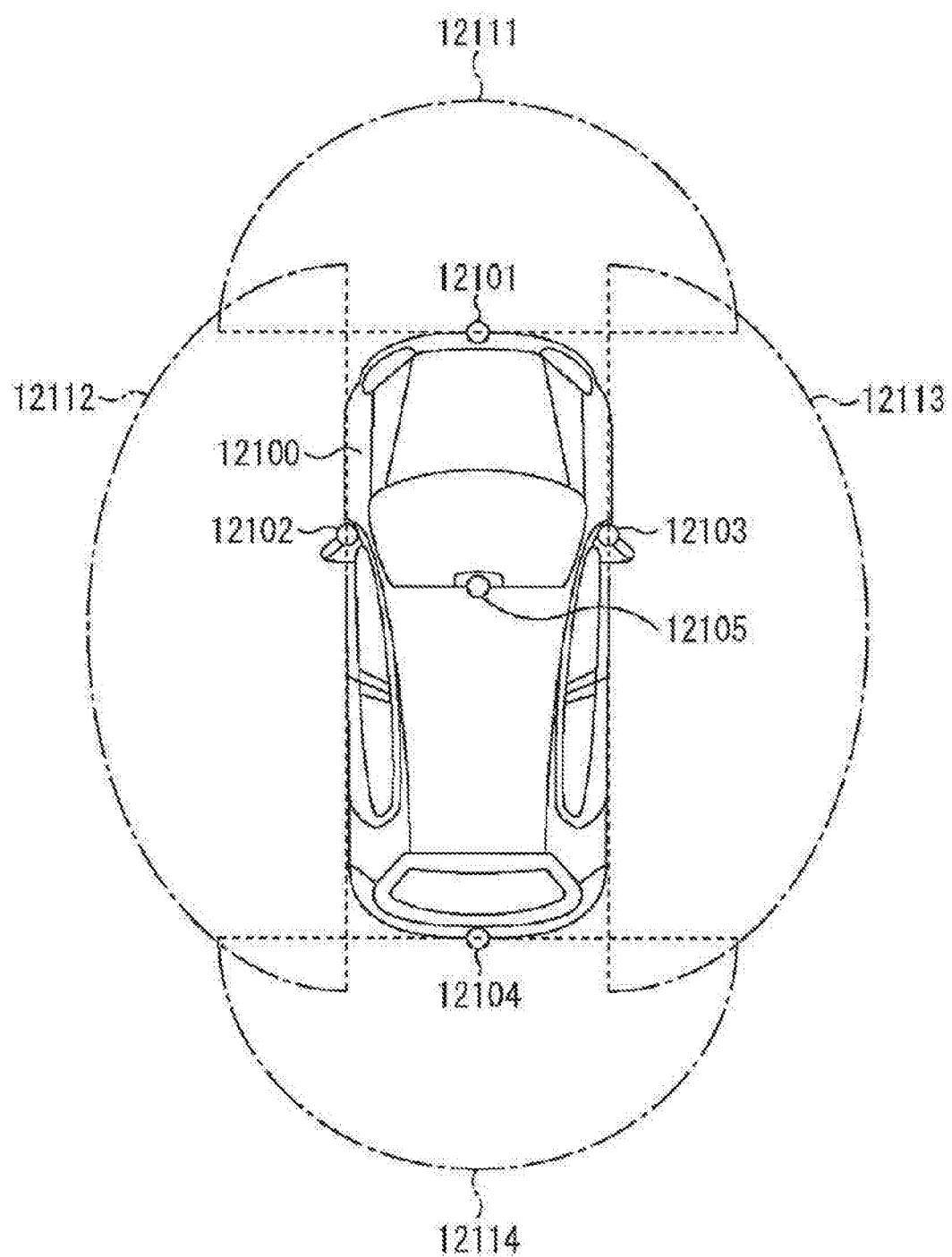

LIGHT-RECEIVING DEVICE, METHOD OF MANUFACTURING LIGHT-RECEIVING DEVICE, AND ELECTRONIC APPARATUS

CROSS REFERENCE TO RELATED APPLICATIONS

This application is a U.S. National Phase of International Patent Application No. PCT/JP2017/036431 filed on Oct. 6, 2017, which claims priority benefit of Japanese Patent Application No. JP 2016-220762 filed in the Japan Patent Office on Nov. 11, 2016. Each of the above-referenced applications is hereby incorporated herein by reference in its entirety.

TECHNICAL FIELD

The present disclosure relates to a light-receiving device used in, for example, an infrared sensor, etc. and a manufacturing method thereof, and to an electronic apparatus.

BACKGROUND ART

Because of high quantum conversion efficiency in an infrared region, an InGaAs film is expected as a photoelectric conversion film for a next-generation image sensor. For example, PTL 1 discloses a light-receiving device that uses the InGaAs film as a light-receiving layer. In the light-receiving device, the InGaAs film is formed on an InP substrate by Epi growth.

Incidentally, increasing a diameter of an InP wafer, which is a base for the Epi growth of the InGaAs film, has not advanced due to a technical issue or high wafer cost. Accordingly, a method of increasing the diameter of the InP wafer by forming the InP film on an Si wafer is under development. As a method of forming an InP film on the Si wafer and further forming on the InP film the InGaAs film having high crystalline nature by means of the Epi growth, an ART (Aspect Ratio Trapping) process is under development.

CITATION LIST

Patent Literature

PTL 1: Japanese Unexamined Patent Application Publication No. S63-160283

SUMMARY OF THE INVENTION

Incidentally, a CMOS (Complementary Metal Oxide Semiconductor) image sensor including a light-receiving device described above is requested to suppress generation of a dark current.

It is desirable to provide a light-receiving device that is able to suppress generation of a dark current, a method of manufacturing the light-receiving device, and an electronic apparatus.

A light-receiving device according to an embodiment of the present disclosure includes: a photoelectric conversion layer that includes a first compound semiconductor with a first conductivity type and absorbs a wavelength of an infrared region to generate electric charges; a first semiconductor layer formed on the photoelectric conversion layer; and an insulation layer formed to surround the photoelectric conversion layer and the first semiconductor layer, the first semiconductor layer having a second conductivity-type region at a middle region excluding a periphery facing the photoelectric conversion layer.

A method of manufacturing a light-receiving device according to an embodiment of the present disclosure includes: forming a photoelectric conversion layer that includes a first compound semiconductor with a first conductivity type and absorbs a wavelength of an infrared region to generate electric charges; forming a first semiconductor layer on the photoelectric conversion layer; forming an insulation layer surrounding the photoelectric conversion layer and the first semiconductor layer; and forming a second conductivity-type region at a middle region of the first semiconductor layer, excluding a periphery facing the photoelectric conversion layer.

In the light-receiving device and the method of manufacturing the light-receiving device according to the respective embodiments of the present disclosure, the first semiconductor layer is provided on the photoelectric conversion layer including the first compound semiconductor with the first conductivity type, and the second conductivity-type region is formed on the middle region of the first semiconductor layer, excluding the periphery facing the photoelectric conversion layer. This makes it possible to form a p-n junction having fewer crystal defects.

An electronic apparatus according to an embodiment of the present disclosure includes the foregoing light-receiving device according to the embodiment of the present disclosure.

According to the light-receiving device, the method of manufacturing the light-receiving device, and the electronic apparatus according to the respective embodiments of the present disclosure, the second conductivity-type region is formed at the middle region of the first semiconductor layer, excluding the periphery facing the photoelectric conversion layer, the photoelectric conversion layer including the first compound semiconductor with the first conductivity type, thus making it possible to form the p-n junction with few crystal defects. Therefore, it is possible to suppress the generation of the dark current.

It is to be noted that the foregoing content is an example of the present disclosure. The effects of the present disclosure are not limited to those described above, and may be other different effects or further include other effects.

BRIEF DESCRIPTION OF DRAWINGS

FIG. 1 is a schematic cross-sectional view of an example of a configuration of a light-receiving device according to an embodiment of the present disclosure.

FIG. 2A is a schematic cross-sectional view of an example of a manufacturing process of the light-receiving device illustrated in FIG. 1.

FIG. 2B is a schematic cross-sectional view of a process following FIG. 2A.

FIG. 2C is a schematic cross-sectional view of a process following FIG. 2B.

FIG. 3A is a schematic cross-sectional view of a process following FIG. 2C.

FIG. 3B is a schematic cross-sectional view of a process following FIG. 3A.

FIG. 3C is a schematic cross-sectional view of a process following FIG. 3B.

FIG. 4A is a schematic cross-sectional view of a process following FIG. 3C.

FIG. 4B is a schematic cross-sectional view of a process following FIG. 4A.

FIG. 5A is a schematic cross-sectional view of a process following FIG. 4B.

FIG. 5B is a schematic cross-sectional view of a process following FIG. 5A.

FIG. 6 is a schematic cross-sectional view of a process following FIG. 5B.

FIG. 7 is a schematic cross-sectional view of an example of a configuration of a light-receiving device according to Modification Example of the present disclosure.

FIG. 8 is a block diagram illustrating a configuration of an imaging apparatus.

FIG. 9 is a functional block diagram illustrating an example of an electronic apparatus (camera) using the imaging apparatus illustrated in FIG. 8.

FIG. 10 is a block diagram illustrating an example of a schematic configuration of an in-vivo information acquisition system.

FIG. 11 is a block diagram illustrating an example of a schematic configuration of a vehicle control system.

FIG. 12 is an explanatory diagram of an example of an installation position of an imaging unit.

MODES FOR CARRYING OUT THE INVENTION

In the following, some embodiments of the present disclosure are described in detail with reference to the drawings. It is to be noted that description is given in the following order. It is to be noted that the embodiments described below each illustrate a specific example of the present disclosure, and the present disclosure is not limited to the following embodiments. Moreover, the present disclosure is not limited to positions, dimensions, dimension ratios, and other factors of respective components illustrated in the drawings. It is to be noted that description is given in the following order.
1. Embodiment (An example of a light-receiving device selectively having a second conductivity-type region at a middle region of a first semiconductor layer)
1-1. Configuration of the light-receiving device
1-2. Method of manufacturing the light-receiving device
1-3. Workings and effects
2. Modification Example
3. Application Examples
Application Example 1 (An example of an imaging apparatus)
Application Example 2 (An example of an electronic apparatus)
Application Example 3 (An example of an in-vivo information acquisition system)
Application Example 4 (An example of a mobile object control system)

1. Embodiment

FIG. 1 illustrates a cross-sectional configuration of a light-receiving device (light-receiving device 10A) according to an embodiment of the present disclosure. The light-receiving device 10A is provided on each of a plurality of two-dimensionally disposed light-receiving unit regions (referred to as pixels P), for example. The light-receiving device 10A has, for example, a photoelectric conversion function to a wavelength of a short infrared region (780 nm or higher and less than 2500 nm, for example). The light-receiving device 10A is applied to an infrared sensor, for example.

(1-1. Configuration of Light-Receiving Device)

The light-receiving device 10A is formed for each of the pixels P, for example and has a configuration in which a photoelectric conversion layer 22 and a first semiconductor layer 23, for example, are stacked in this order on side of a surface of a second semiconductor layer 21 (surface (rear surface S2) on opposite side to a light-entering surface S1). A second conductivity-type region 23A is formed in a selective region of the first semiconductor layer 23. A side surface of the second semiconductor layer 21, a side surface of the photoelectric conversion layer 22, and a side surface of the first semiconductor layer 23 are surrounded by an insulation layer 24, which separates each light-receiving device 10A from each pixel P. The insulation layer 24 further extends on side of the rear surface S2, covering a surface of the first semiconductor layer 23 (surface on opposite side to a surface facing the photoelectric conversion layer). In the insulation layer 24 covering the surface of the first semiconductor layer 23, an opening 24H is provided at position corresponding to the second conductivity-type region 23A of the first semiconductor layer 23. A metal film is embedded in the opening 24H, forming a contact electrode 25. A semiconductor substrate 20 ranges from the second semiconductor layer 21 to the contact electrode 25. On side of the light-entering surface S1 of the semiconductor substrate 20 is provided an on-chip lens 41 for each of the pixels P, for example. Furthermore, to side of the rear surface S2 of the semiconductor substrate 20 is laminated a multilayer wiring substrate 30 having a readout circuit via an insulation layer 37. In the following, description is given of respective units.

The second semiconductor layer 21 is configured by a group III-V semiconductor of an n-type or an i-type (intrinsic semiconductor), for example. Although the photoelectric conversion layer 22 is formed to be in contact with the second semiconductor layer 21 on the side of the rear surface S2, other layers may also intermediate between the second semiconductor layer 21 and the photoelectric conversion layer 22. Although examples of the material intermediating between the second semiconductor layer 21 and the photoelectric conversion layer 22 include a compound semiconductor including InAlAs, Ge, Si, GaAs, InP, InGaAsP, AlGaAs, it is desirable that a material lattice-matched between the second semiconductor layer 21 and the photoelectric conversion layer 22 be selected.

The photoelectric conversion layer 22 includes a compound semiconductor that absorbs a wavelength of an infrared region (hereinafter referred to as infrared rays), for example, and generates electric charges (electron and hole). The compound semiconductor used for the photoelectric conversion layer 22 is, for example, the group III-V semiconductor and includes $In_xGa_{(1-x)}As$ (x:0<x≤1), for example. To be more sensitive in the infrared region, however, it is desirable that x≥0.4. Examples of composition of the compound semiconductor of the photoelectric conversion layer 22 that is lattice-matched with the second semiconductor layer 21 configured by InP include $In_{0.53}Ga_{0.47}As$.

The compound semiconductor that configures the photoelectric conversion layer 22 has the n-type conductivity type (first conductivity type), for example, and forms a p-n junction through lamination with the first semiconductor layer 23 having the second conductivity-type region 23A.

The first semiconductor layer 23 is provided to be in contact with opposite side (side of the rear surface S2) to side of the second semiconductor layer 21 of the photoelectric conversion layer 22. It is desirable that the first semiconductor layer 23 include the compound semiconductor having a larger bandgap than that of the photoelectric conversion layer 22. Examples of the compound semiconductor having the larger bandgap than $In_{0.53}Ga_{0.47}As$ (bandgap of 0.74 eV) include InP (bandgap of 1.34 eV) or InAlAs, etc.

The second conductivity-type region 23A is formed in a selective region on the first semiconductor layer 23. Specifically, the second conductivity-type region 23A is formed in the middle region excluding the periphery facing the photoelectric conversion layer. The range of the periphery is 100 nm, for example, from the side surface of the first semiconductor layer 23, and the second conductivity-type region is formed in a region which is 100 nm inside from the side surface of the first semiconductor layer 23.

The second conductivity-type region 23A is a region including, for example, p-type impurities (p-type impurity region). Examples of the p-type impurities include zinc (Zn), cadmium (Cd), and beryllium (Be), etc. It is to be noted that a portion of the p-type impurity region forming the second conductivity-type region 23A may extend to the photoelectric conversion layer 22.

The insulation layer 24 is formed by using inorganic insulating materials, for example. Examples of the inorganic insulating materials include silicon nitride (SiN), aluminum oxide ($Al_2O_3$), silicon oxide ($SiO_2$), and hafnium oxide ($HfO_2$). The insulation layer 24 includes one or more kinds of silicon nitride (SiN), aluminum oxide ($Al_2O_3$), silicon oxide ($SiO_2$), and hafnium oxide ($HfO_2$). As descried above, the insulation layer 24 is formed to surround the side surface of the second semiconductor layer 21, the side surface of the photoelectric conversion layer 22, and the side surface of the first semiconductor layer 23, which electrically separates adjacent pixels P. The insulation layer 24 further extends to the side of the rear surface S2 and covers the one surface of the first semiconductor layer 23 (surface on opposite side to the surface facing the photoelectric conversion layer 22). On the insulation layer 24, the opening 24H is formed at a position facing the second conductivity-type region 23A of the first semiconductor layer 23.

The contact electrode 25 is an electrode to which a voltage for reading out electric charges (holes, for example), as signal charges, that are generated in the photoelectric conversion layer 22 is supplied. The contact electrode 25 is formed for each pixel P. Examples of constituent materials of the contact electrode 25 include an elementary substance of any of, for example, copper (Cu), titanium (Ti), tungsten (W), titanium nitride (TiN), platinum (Pt), gold (Au), germanium (Ge), palladium (Pd), zinc (Zn), nickel (Ni), and aluminum (Al), or an alloy including one or more kind thereof. The contact electrode 25 may be a monolayer film of the foregoing constituent materials or may be formed as a laminated film that combines two or more kinds thereof, for example.

The contact electrode 25 buries the opening 24H and is electrically coupled to the second conductivity-type region 23A of the first semiconductor layer 23. Here, the contact electrode 25 embeds the opening 24H and is in direct contact with the second conductivity-type region 23A. It is to be noted that for the contact electrode 25, as in the present embodiment, one contact electrode 25 may be disposed for one pixel P or a plurality of the contact electrodes 25 may be disposed for one pixel P. In addition, in a case where the plurality of the contact electrodes 25 are disposed for the one pixel P, some of the contact electrodes 25 may include an electrode (dummy electrode) that does not actually contribute to fetching of the electric charges.

An insulation layer 37 is provided between the semiconductor substrate 20 and the multilayer wiring substrate 30. On the insulation layer 37, for example, a coupling layer 38 that projects (protruding) to the X axis direction than to a side surface of the opening 24H is provided between the contact electrode 25 provided on the semiconductor substrate 20 and a readout electrode 36 provided on the multilayer wiring substrate 30. More specifically, the coupling layer 38 is formed in a canopy shape on an upper part of the contact electrode 25 (rear surface S2 side) and on an upper part of the readout electrode 36 (light-entering surface S1 side). The coupling layer 38 serves to electrically couple the contact electrode 25 and the readout electrode 36.

The multilayer wiring substrate 30 has an inter-layer insulation layer 32 formed on a support substrate 31 configured by Si, for example. The readout circuit for reading a signal from each of the pixels P is formed with the inter-layer insulation layer 32 in between. The readout circuit is configured by a pixel circuit 35 and a wiring layer 34 having various types of wires 34A, 34B, and 34C. The pixel circuit 35 and the various types of wires 34A, 34B, and 34C are electrically coupled by penetration electrodes 33A, 33B, 33C, and 33D, respectively. The readout electrode 36 is provided on the pixel circuit 35 and electrically coupled to the pixel circuit 35. The readout electrode 36 is electrically coupled to the contact electrode 25 via the coupling layer 38. This allows the electric charges (holes, for example) generated in the photoelectric conversion layer 22 to be read out for each of the pixels P.

The on-chip lens 41 has a function to focus light to the photoelectric conversion layer 22. Lens materials include an organic material or a silicon oxide film ($SiO_2$ film), etc. Although FIG. 1 illustrates a case where the on-chip lens 41 is provided for each of the pixels P, a configuration is not limited thereto and one on-chip lens 41 may be formed for the plurality of pixels P.

(1-2. Method of Manufacturing Light-Receiving Device)

The light-receiving device 10A may be manufactured in the following manner, for example. An example of manufacturing processes of the light-receiving device 10A is illustrated in an order of processes in of FIGS. 2A, 2B, 2C, 3A, 3B, 3C, 4A, 4B, 5A, 5B, and FIG. 6.

First, as illustrated in FIG. 2A, a film of an insulation layer 24A configured by $SiO_2$, for example, is formed on a surface of an Si substrate 51, for example, by means of CVD (Chemical Vapor Deposition), for example. Thereafter, the insulation layer 24A is partially removed by means of a lithography method and dry etching or wet etching, for example, to form an opening 51H and expose the Si substrate. Then, etching is performed so as to create a quadrangular pyramid shape (111) surface in a concave direction on the Si substrate 51 by wet processing, for example. Subsequently, as illustrated in FIG. 2B, from the Si (111) surface, the second semiconductor layer 21A including InP, for example, is selectively Epi-grown along the (111) surface, by means of a metal organic chemical vapor deposition (MOCVD), for example. Thereafter, as illustrated in FIG. 2C, the insulation layer 24A and the second semiconductor layer 21A are planarized by means of CMP (Chemical Mechanical Polishing), for example.

Subsequently, as illustrated in FIG. 3A, after a film of an insulation layer 24B configured by $SiO_2$, for example, is formed on the insulation layer 24A and the second semiconductor layer 21A, an opening 24BH having a same shape as the opening 51H is formed. Thereafter, a semiconductor layer 22A including InGaAs, for example, is Epi-grown on the second semiconductor layer 21A in the opening 24BH. Subsequently, as illustrated in FIG. 3B, the insulation layer 24B and the semiconductor layer 22A are planarized by means of the CMP, for example. This forms the photoelectric conversion layer 22 on the second semiconductor layer 21A.

It is to be noted that in a growth process of the second semiconductor layer 21A and the semiconductor layer 22A, by introduction of gas, etc., including the n-type impurities, for example, a film of the second semiconductor layer 21A and a film of the semiconductor layer 22A are each formed as the conductivity-type layer of the n-type.

Subsequently, as illustrated in FIG. 3C, the first semiconductor layer 23 including InP, for example, is Epi-grown on the photoelectric conversion layer 22 including InGaAs. With the above, during the Epi growth, crystal defects in the second semiconductor layer 21A, the semiconductor layer 22A, and the first semiconductor layer 23 terminate on side walls of the insulation layer 24A and an insulation layer 25B. This forms the film of the second semiconductor layer 21A, the film of the semiconductor layer 22A, and a film of the first semiconductor layer 23 that have high crystalline nature.

Subsequently, as illustrated in FIG. 4A, after a film of an insulation layer 24C configured by $SiO_2$, for example, is formed on the insulation layer 24B and the first semiconductor layer 23, the opening 24H is formed on the first semiconductor layer 23. As illustrated in FIG. 4A, a position where the opening 24H is formed is the middle region excluding the periphery of the first semiconductor layer 23. Then, for example, the p-type impurities (zinc (Zn), for example) are diffused from the opening 24H to the first semiconductor layer 23 by vapor-phase diffusion, for example. This forms a diffusion region of Zn (second conductivity-type region 23A) on the first semiconductor layer 23.

Subsequently, as illustrated in FIG. 5A, by means of a damascene method, Cu, for example, is buried in the opening 24H to form the contact electrode 25. It is to be noted that at this time, the contact electrode 25 may be formed by forming a Cu film by means of a vapor deposition method, a PVD method or a plating method, etc., for example and then polishing a surface of the Cu film by means of the CMP method, for example. Thereafter, as illustrated in FIG. 5B, the semiconductor substrate 20 is inverted and laminated to the multilayer wiring substrate 30 having the insulation layer 37 that is separately formed and has the coupling layer 38 embedded in a top face. The contact electrode 25, specifically, the contact electrode 25 on side of the semiconductor substrate 25, is metal joined with the coupling layer 38 provided on side of the multilayer wiring substrate 30 to electrically couple to each other. Examples of metal joining methods include a plasma joining, normal temperature joining, thermal diffusion joining, etc. Alternatively, the contact electrode 25 and the coupling layer 38 may be coupled by a bump.

Subsequently, as illustrated in FIG. 6, the Si substrate 51 is removed and the insulation layer 24A and the second semiconductor layer 21A are polished to expose the second semiconductor layer 21A. Lastly, the on-chip lens 41 is formed on the insulation layer 24 and the side of the light-entering surface S1 of the second semiconductor layer 21. This completes the light-receiving device 10A illustrated in FIG. 1.

(1-3. Workings and Effects)

As described above, an InGaAs film is expected as a photoelectric conversion film for a next-generation image sensor because of high quantum conversion efficiency in an infrared region, and methods of forming the InGaAs film on the InP substrate by the Epi growth are under development. Of the methods, as a method of increasing the diameter of the InP substrate and forming the InGaAs film having high crystalline nature, an ART (Aspect Ratio Trapping) process is under development. In the ART process, similarly to a mesa-type photodiode structure, the pixels are separated by the insulation film, thus making it possible to physically separate the adjacent pixels. Therefore, it is possible to reduce generation of crosstalk, as compared to a planar-type photodiode to be separated by an impurity layer.

In addition, in the ART process, the InP film and the InGaAs film are Epi-grown in sequence from an opening provided on an Si wafer, thus making it possible to terminate the crystal defects on the side surfaces of the respective semiconductor films. Hence, the crystalline nature at the middle region of the InP film and the InGaAs film is improved. However, the crystal defects still remain in the periphery of the InP film and the InGaAs film. The crystal defects cause deterioration in an interface state or lifetime of electric charges. The deterioration in the interface state or the lifetime of electric charges causes generation of a dark current in an image sensor, etc., and generates noise. Therefore, it is desirable to remove the crystal defects formed in the periphery. In the ART process, however, the side surface of the InP film and the side surface of the InGaAs film are covered with the insulation film, which thus makes it difficult to remove only the crystal defects in the periphery.

In contrast, in the light-receiving device 10A and the manufacturing method thereof of the present embodiment, the first semiconductor layer 23 including InP is provided on the photoelectric conversion layer 22, the photoelectric conversion layer 22 including InGaAs with the first conductivity type (n-type, for example). The opening 24H having the diameter smaller than the area of the first semiconductor layer 23 is provided on the insulation layer 24 on the first semiconductor layer 23. Through the opening 24H, the first semiconductor layer 23 is doped with, for example, the p-type impurities (Zn, for example). This forms the second conductivity-type region 23A at the middle region with few crystal defects, exclusive of the periphery of the first semiconductor layer 23 that includes many crystal defects. Therefore, it is possible to form a p-n junction interface with few crystal defects.

As described above, in the present embodiment, on the insulation layer 24 on the first semiconductor layer 23, the opening 24H is provided at the middle region of the first semiconductor layer 23, the opening 24H having the diameter smaller than the area of the first semiconductor layer 23. Through the opening 24H, the first semiconductor layer 23 is doped with the p-type impurities to form the second conductivity-type region 23A. This makes it possible to form the p-n junction interface with few crystal defects between the photoelectric conversion layer 22 of the first conductivity type (n-type, for example) and the second conductivity-type region 23 of the first semiconductor layer 23. Therefore, it is possible to provide the light-receiving device with which the generation of noise causing the dark current is suppressed and that is able to improve the image quality, as well as an electronic apparatus including an imaging device equipped with the light-receiving device.

A modification example of the foregoing embodiment is described hereinafter. In the following, same components as those of the foregoing embodiment are denoted by same reference numerals, and description thereof is omitted where appropriate.

2. Modification Example

FIG. 7 illustrates a cross-sectional configuration of a light-receiving device (light-receiving device 10B) according to Modification Example of the present disclosure. Similarly to the light-receiving device 10A of the foregoing embodiment, the light-receiving device 10B of the Modification Example is provided in each of the plurality of two-dimensionally deposited light-receiving unit areas (referred to as pixels P). The light-receiving device 10B in the Modification Example differs from the foregoing embodiment in that the light-receiving device 10B includes a transparent electrode 42, a protection layer 43, and color filters 44 between the light-entering surface S1 side of the semiconductor substrate 20 and the on-chip lens 41.

The transparent electrode 42 is formed as, for example, an electrode common to the respective pixels on the light-entering surface S1 of the semiconductor substrate 20. The transparent electrode 42 is electrically coupled to the semiconductor substrate 20 and may discharge the electrons, for example, through the transparent electrode 42, in a case where the holes, for example, of the electric charges generated in the photoelectric conversion layer 22 are read out as the signal charges through the contact electrode 25. In addition, in the Modification Example, provision of the transparent electrode 42 makes it easier to form a larger potential gradient in the photoelectric conversion layer 22.

Examples of the constituent materials of the transparent electrode 42 include the elementary substance of any of, for example, titanium (Ti), tungsten (W), titanium nitride (TiN), platinum (Pt), gold (Au), germanium (Ge), nickel (Ni), and aluminum (Al), or an alloy including one or more kind thereof. Of these constituent materials, indium titanium oxide (ITiO), in particular, is highly transparent to the infrared region and is desirable as the constituent material of the transparent electrode 42. In addition to the materials listed above, examples of the transparent electrode 42 include indium tin oxide (ITO) or tin (Sn), tin oxide ($SnO_2$), IWO, indium-zinc based multiple oxide (IZO), zinc-doped aluminum oxide (AZO), zinc-doped gallium oxide (GZO), aluminum oxide doped with magnesium and zinc (AlMgZnO), indium-gallium multiple oxide (IGO), In—GaZnO$_4$ (IGZO), fluorine-doped indium oxide (IFO), antimony-doped tin oxide (ATO), fluorine-doped tin oxide (FTO), zinc oxide (ZnO), boron-doped ZnO, and InSnZnO, etc.

The protection layer 43 is to planarize a surface of the transparent electrode 42 and formed using the inorganic insulating material, for example. Examples of the inorganic insulating materials include silicon nitride (SiNx), silicon oxide (SiOx), aluminum oxide ($Al_2O_3$), and hafnium oxide ($HfO_2$). The protection layer 43 includes one or more kind thereof.

The color filter 44 is provided on the protection layer 43, and any of a red filter (44R), a green filter (44G), a blue filter (44B), and an IR filter (44I) is disposed on each of the pixels P. The color filters 44 are provided in a regular color array (Bayer array, for example). Provision of such color filters 44 allows the light-receiving device 10B to obtain light reception data of a wavelength corresponding to the color array. That is, the light-receiving device 10B in the Modification Example has the photoelectric conversion function for wavelengths from a visible region (380 nm or higher and less than 780 nm, for example) to the short infrared region (780 nm or higher and less than 2400 nm, for example).

3. Application Examples

Application Example 1

FIG. 8 illustrates a functional configuration of an imaging apparatus (imaging apparatus 1) that uses a device structure of an imaging device as the light-receiving device 10A (or the light-receiving device 10B) described in the foregoing embodiment, etc. The imaging apparatus 1 is, for example, an infrared image sensor having a pixel unit 1a and a peripheral circuit 230 that drives the pixel unit 1a, for example. The peripheral circuit 230 includes a row scanning unit 231, a horizontal selection unit 233, a column scanning unit 234, and a system control unit 232, for example.

The pixel unit 1a has the plurality of pixels P that are two-dimensionally disposed in a matrix shape, for example. To the pixels P are wired pixel drive lines Lread (row selection line and reset control line, for example) for respective pixel rows, for example, and are wired vertical signal lines Lsig for respective pixel columns. The pixel drive lines Lread are to transmit a drive signal for reading a signal from each of the pixels P. One end of each of the pixel drive lines Lread is coupled to an output end corresponding to each row of the row scanning unit 231.

The row scanning unit 231 is a pixel drive unit configured by a shift register or an address decoder, etc., and driving each of the pixels P of the pixel unit 1a in a unit of the row, for example. A signal outputted from each of the pixels P of the pixel row selected and scanned by the row scanning unit 231 is supplied to the horizontal selection unit 233 through each of the vertical signal lines Lsig. The horizontal selection unit 233 is configured by an amplifier or a horizontal selection switch, etc. provided for each of the vertical signal lines Lsig.

The column scanning unit 234 is configured by the shift register or the address decoder or the like and drives each horizontal selection switch of the horizontal selection unit 233 in sequence, while scanning the horizontal selection switch. With the selective scanning of the column scanning unit 234, a signal of each of the pixels transmitted through each of the vertical signal lines Lsig is outputted to a horizontal signal line 235 in sequence and inputted to an unillustrated signal processing unit, etc., through the horizontal signal line 235.

The system control unit 232 receives a clock given from outside or data that commands an operating mode, etc., and also outputs data such as internal information of the imaging apparatus 1. The system control unit 232 further includes a timing generator generating various types of timing signals, and performs drive control of the row scanning unit 231, the horizontal selection unit 233, and the column scanning unit 234, etc., on the basis of the various types of timing signals generated by the timing generator.

Application Example 2

The foregoing imaging apparatus 1 may be applied to various types of electronic apparatuses such as a camera that is able to image the infrared region, for example, etc. FIG. 9 illustrates a schematic configuration of an electronic apparatus 2 (camera) as an example thereof. The electronic apparatus 2 is a camera that is able to shoot a static image or a moving image, and includes the imaging apparatus 1, an optical system (optical lens) 310, a shutter apparatus 311, a drive unit 313 for driving the imaging apparatus 1 and the shutter apparatus 311, and a signal processing unit 312.

The optical system 310 is to guide image light (entering light) from an object to the imaging apparatus 1. The optical system 310 may be configured by a plurality of optical lenses. The shutter apparatus 311 is to control a light application period to the imaging apparatus 1 and a light-shielding period. The drive unit 313 is to control a transfer operation of the imaging apparatus 1 and a shutter operation of the shutter apparatus 311. The signal processing unit 312 is to perform various types of signal processing on a signal outputted from the imaging apparatus 1. An image signal Dout after signal processing is stored in a storage medium such as a memory, etc., or outputted to the monitor, etc.

Furthermore, it is also possible to apply the light-receiving device 10A (or the light-receiving device 10B) described in the present embodiment to the following electronic apparatuses (capsule type endoscope 10100 and a mobile object such as a vehicle).

Application Example 3

<Industrial Application Example to an In-Vivo Information Acquisition System>

FIG. 10 is a block diagram depicting an example of a schematic configuration of an in-vivo information acquisition system of a patient using a capsule type endoscope, to which the technology according to an embodiment of the present disclosure (present technology) can be applied.

The in-vivo information acquisition system 10001 includes a capsule type endoscope 10100 and an external controlling apparatus 10200.

The capsule type endoscope 10100 is swallowed by a patient at the time of inspection. The capsule type endoscope 10100 has an image pickup function and a wireless communication function and successively picks up an image of the inside of an organ such as the stomach or an intestine (hereinafter referred to as in-vivo image) at predetermined intervals while it moves inside of the organ by peristaltic motion for a period of time until it is naturally discharged from the patient. Then, the capsule type endoscope 10100 successively transmits information of the in-vivo image to the external controlling apparatus 10200 outside the body by wireless transmission.

The external controlling apparatus 10200 integrally controls operation of the in-vivo information acquisition system 10001. Further, the external controlling apparatus 10200 receives information of an in-vivo image transmitted thereto from the capsule type endoscope 10100 and generates image data for displaying the in-vivo image on a display apparatus (not depicted) on the basis of the received information of the in-vivo image.

In the in-vivo information acquisition system 10001, an in-vivo image imaged a state of the inside of the body of a patient can be acquired at any time in this manner for a period of time until the capsule type endoscope 10100 is discharged after it is swallowed.

A configuration and functions of the capsule type endoscope 10100 and the external controlling apparatus 10200 are described in more detail below.

The capsule type endoscope 10100 includes a housing 10101 of the capsule type, in which a light source unit 10111, an image pickup unit 10112, an image processing unit 10113, a wireless communication unit 10114, a power feeding unit 10115, a power supply unit 10116 and a control unit 10117 are accommodated.

The light source unit 10111 includes a light source such as, for example, a light emitting diode (LED) and irradiates light on an image pickup field-of-view of the image pickup unit 10112.

The image pickup unit 10112 includes an image pickup element and an optical system including a plurality of lenses provided at a preceding stage to the image pickup element. Reflected light (hereinafter referred to as observation light) of light irradiated on a body tissue which is an observation target is condensed by the optical system and introduced into the image pickup element. In the image pickup unit 10112, the incident observation light is photoelectrically converted by the image pickup element, by which an image signal corresponding to the observation light is generated. The image signal generated by the image pickup unit 10112 is provided to the image processing unit 10113.

The image processing unit 10113 includes a processor such as a central processing unit (CPU) or a graphics processing unit (GPU) and performs various signal processes for an image signal generated by the image pickup unit 10112. The image processing unit 10113 provides the image signal for which the signal processes have been performed thereby as RAW data to the wireless communication unit 10114.

The wireless communication unit 10114 performs a predetermined process such as a modulation process for the image signal for which the signal processes have been performed by the image processing unit 10113 and transmits the resulting image signal to the external controlling apparatus 10200 through an antenna 10114A. Further, the wireless communication unit 10114 receives a control signal relating to driving control of the capsule type endoscope 10100 from the external controlling apparatus 10200 through the antenna 10114A. The wireless communication unit 10114 provides the control signal received from the external controlling apparatus 10200 to the control unit 10117.

The power feeding unit 10115 includes an antenna coil for power reception, a power regeneration circuit for regenerating electric power from current generated in the antenna coil, a voltage booster circuit and so forth. The power feeding unit 10115 generates electric power using the principle of non-contact charging.

The power supply unit 10116 includes a secondary battery and stores electric power generated by the power feeding unit 10115. In FIG. 10, in order to avoid complicated illustration, an arrow mark indicative of a supply destination of electric power from the power supply unit 10116 and so forth are omitted. However, electric power stored in the power supply unit 10116 is supplied to and can be used to drive the light source unit 10111, the image pickup unit 10112, the image processing unit 10113, the wireless communication unit 10114 and the control unit 10117.

The control unit 10117 includes a processor such as a CPU and suitably controls driving of the light source unit 10111, the image pickup unit 10112, the image processing unit 10113, the wireless communication unit 10114 and the power feeding unit 10115 in accordance with a control signal transmitted thereto from the external controlling apparatus 10200.

The external controlling apparatus 10200 includes a processor such as a CPU or a GPU, a microcomputer, a control board or the like in which a processor and a storage element such as a memory are mixedly incorporated. The external controlling apparatus 10200 transmits a control signal to the control unit 10117 of the capsule type endoscope 10100 through an antenna 10200A to control operation of the capsule type endoscope 10100. In the capsule type endoscope 10100, an irradiation condition of light upon an observation target of the light source unit 10111 can be changed, for example, in accordance with a control signal from the external controlling apparatus 10200. Further, an image pickup condition (for example, a frame rate, an exposure value or the like of the image pickup unit 10112) can be changed in accordance with a control signal from the external controlling apparatus 10200. Further, the substance of processing by the image processing unit 10113 or a condition for transmitting an image signal from the wireless communication unit 10114 (for example, a transmission interval, a transmission image number or the like) may be changed in accordance with a control signal from the external controlling apparatus 10200.

Further, the external controlling apparatus 10200 performs various image processes for an image signal transmitted thereto from the capsule type endoscope 10100 to generate image data for displaying a picked up in-vivo image on the display apparatus. As the image processes, various signal processes can be performed such as, for example, a development process (demosaic process), an image quality improving process (bandwidth enhancement process, a super-resolution process, a noise reduction (NR) process and/or image stabilization process) and/or an enlargement process (electronic zooming process). The external controlling apparatus 10200 controls driving of the display apparatus to cause the display apparatus to display a picked up in-vivo image on the basis of generated image data. Alternatively, the external controlling apparatus 10200 may also control a recording apparatus (not depicted) to record generated image data or control a printing apparatus (not depicted) to output generated image data by printing.

As described, description is given above of an example of the in-vivo information acquisition system to which the technology of the present disclosure can be applied. Of the configurations described above, the technology according to the present disclosure can be applied to, for example, the image pickup unit 10112. This makes it possible to obtain a clear image of an operated site, leading to the improvement of accuracy of examination.

Application Example 4

<Industrial Application Example to a Mobile Object Control System>

The technology according to the present disclosure (the present technology) is applicable to various products. For example, the technology according to the present disclosure may be realized as an apparatus mounted to any kind of moving bodies such as a vehicle, an electric vehicle, a hybrid electric vehicle, a motorcycle, a bicycle, a personal mobility, an aircraft, a drone, a watercraft, and a robot.

FIG. 11 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 11, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 11, an audio speaker 12061, a display section 12062, and an instrument panel 12063 are illustrated as the output device. The display section 12062 may, for example, include at least one of an on-board display and a head-up display.

FIG. 12 is a diagram depicting an example of the installation position of the imaging section 12031.

In FIG. 12, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 12 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

Description has been given of an example of the vehicle control system to which the technology according to the present disclosure is applicable. The technology according to the present disclosure may be applicable to an imaging section 12031, etc., for example, of the configurations described above. Application of the technology according to the present disclosure to the imaging unit 12031 makes it possible to obtain a taken image that is easier to view, thus allowing for alleviation of fatigue of a driver.

Although description has been given with reference to the embodiments, the modification example, and the application examples, contents of the present disclosure are not limited to the foregoing embodiments, etc., and may be modified in a variety of ways. For example, a layer configuration of the light-receiving device 10A (or the light-receiving device 10B) described in the foregoing embodiments, etc., is an example and may further include other layers. In addition, the materials or the thicknesses of the respective layers are merely an example and not limited to those descried above.

Furthermore, in the foregoing embodiment, etc., although the example is illustrated in which the second semiconductor layer 21 and the photoelectric conversion layer 22 are the n-type conductivity type, and the p-type conductivity-type region (second conductivity-type region 23A) is provided in the first semiconductor layer 23, the example is not limited thereto, the second semiconductor layer 21 and the photoelectric conversion layer 22 may be the p-type conductivity type and the second conductivity-type region 23A of the first semiconductor layer 23 may be the n-type conductivity type.

In addition, the effects described in the foregoing embodiment, etc. are merely an example and may be other effects or may further include other effects.

Moreover, the technology may have the following configurations.

(1)
A light-receiving device including:
a photoelectric conversion layer that includes a first compound semiconductor with a first conductivity type and absorbs a wavelength of an infrared region to generate electric charges;
a first semiconductor layer formed on the photoelectric conversion layer; and
an insulation layer formed to surround the photoelectric conversion layer and the first semiconductor layer, in which
the first semiconductor layer includes a second conductivity-type region at a middle region excluding a periphery facing the photoelectric conversion layer.

(2)
The light-receiving device according to (1) including:
an opening at a position facing the second conductivity-type region on the first semiconductor layer, in which
the insulation layer is formed to surround side surfaces of the photoelectric conversion layer and the first semiconductor layer and a top face of the first semiconductor layer.

(3)
The light-receiving device according to (2), in which
a diameter of the opening is smaller than area of the first semiconductor layer.

(4)
The light-receiving device according to any one of (1) to (3), in which
the photoelectric conversion layer includes a second semiconductor layer on side of a light-entering surface, and
the second semiconductor layer is surrounded by the insulation layer.

(5)
The light-receiving device according to any one of (1) to (4), in which on a surface on opposite side to the light-entering surface of the photoelectric conversion layer, a multilayer wiring substrate is disposed with the first semiconductor layer and the insulation layer in between, the multilayer wiring substrate including a readout circuit.

(6)
The light-receiving device according to any of (2) to (5) including:
the multilayer wiring substrate on a surface on opposite side to the light-entering surface of the photoelectric conversion layer, the multilayer wiring substrate including the readout circuit, in which
an electrically conducting film is buried in the opening, and
the photoelectric conversion layer is electrically coupled to the readout circuit via the electrically conducting film.

(7)
The light-receiving device according to any of (4) to (6), in which the photoelectric conversion layer, the first semiconductor layer, and the second semiconductor layer are each configured by a compound semiconductor.

(8)
The light-receiving device according to (7), in which the compound semiconductor is a group III-V semiconductor.

(9)
The light-receiving device according to any of (4) to (8), in which
the photoelectric conversion layer is configured by $In_xGa_{(1-x)}As$ ($0<x\le1$), and
the first semiconductor layer and the second semiconductor layer are configured by InP.

(10)
The light-receiving device according to any of (1) or (9), in which the insulation film is configured by a silicon nitride ($SiN_x$) film or a silicon oxide ($SiO_x$) film.

(11)
A method of manufacturing a light-receiving device including:
forming a photoelectric conversion layer that includes a first compound semiconductor with a first conductivity type and absorbs a wavelength of an infrared region to generate electric charges;
forming a first semiconductor layer on the photoelectric conversion layer;
forming an insulation layer surrounding the photoelectric conversion layer and the first semiconductor layer; and
forming a second conductivity-type region at a middle region of the first semiconductor layer excluding a periphery facing the photoelectric conversion layer.

(12)
The method of manufacturing the light-receiving device according to (11), in which after the first semiconductor layer is formed, an opening smaller than area of the first semiconductor layer is formed at a position facing the first semiconductor layer of the insulation layer that is provided on the first semiconductor layer.

(13)
The method of manufacturing the light-receiving device according to (12), in which impurities are added to the first semiconductor layer through the opening to form the second conductivity-type region.

(14)
An electronic apparatus including:
a plurality of pixels, the electronic apparatus including:
a photoelectric conversion layer that is provided for each of the plurality of pixels, includes a first compound semiconductor with a first conductivity type, and absorbs a wavelength of an infrared region to generate electric charges;
a first semiconductor layer formed on the photoelectric conversion layer; and an insulation layer formed to surround the first photoelectric conversion layer and the first semiconductor layer, in which the first semiconductor layer includes a second conductivity-type region at a middle region excluding a periphery facing the photoelectric conversion layer.

(15)

The electronic apparatus according to (14), in which the photoelectric conversion layer is separated by the insulation layer for each of the pixels.

This application claims the benefits of Japanese Priority Patent Application No. 2016-220762 filed with the Japan Patent Office on Nov. 11, 2016, the entire content of which is incorporated herein by reference.

It should be understood that those skilled in the art could conceive various modifications, combinations, sub-combinations, and alterations depending on design requirements and other factors, insofar as they are within the scope of the appended claims or the equivalents thereof.

The invention claimed is:

1. A light-receiving device, comprising:
    a photoelectric conversion layer that includes a compound semiconductor with a first conductivity-type, wherein the photoelectric conversion layer is configured to absorb a wavelength of an infrared region to generate electric charges;
    a first semiconductor layer on the photoelectric conversion layer;
    a first insulation layer that surrounds each of the photoelectric conversion layer and the first semiconductor layer, wherein
        the first insulation layer has an opening that faces a middle region of the first semiconductor layer,
        the middle region excludes a periphery of the first semiconductor layer facing the photoelectric conversion layer, and
        the middle region of the first semiconductor layer includes a region of a second conductivity-type;
    a contact electrode coupled to the region of the second conductivity-type;
    a multilayer wiring substrate on a surface opposite to a light-entering surface of the photoelectric conversion layer, wherein the multilayer wiring substrate includes:
        a support substrate;
        an inter-insulation layer on the support substrate;
        a readout circuit within the inter-insulation layer, wherein the readout circuit includes a pixel circuit and a wiring layer; and
        a readout electrode on the pixel circuit;
    a second insulation layer that is above the inter-insulation layer and below each of the first insulation layer and the contact electrode; and
    a coupling layer coupled to the contact electrode, wherein
        the coupling layer is on a face of the second insulating layer,
        the coupling layer projects in an X-axis direction on the second insulation layer,
        the projection of the coupling layer is beyond side surfaces of the opening,
        the coupling layer is configured to readout the electric charges through the contact electrode, and
        the readout electrode is coupled with the contact electrode through the coupling layer.

2. The light-receiving device according to claim 1, wherein the first insulation layer surrounds side surfaces of the photoelectric conversion layer and the first semiconductor layer, and a top face of the first semiconductor layer.

3. The light-receiving device according to claim 2, wherein a diameter of the opening is smaller than an area of the first semiconductor layer.

4. The light-receiving device according to claim 2, wherein
    the contact electrode comprises an electrically conducting film in the opening, and
    the photoelectric conversion layer is electrically coupled to the readout circuit via the electrically conducting film.

5. The light-receiving device according to claim 1, wherein
    the photoelectric conversion layer includes a second semiconductor layer on a side of the light-entering surface of the photoelectric conversion layer, and
    the second semiconductor layer is surrounded by the first insulation layer.

6. The light-receiving device according to claim 5, wherein each of the photoelectric conversion layer, the first semiconductor layer, and the second semiconductor layer is configured by the compound semiconductor.

7. The light-receiving device according to claim 6, wherein the compound semiconductor is a group III-V semiconductor.

8. The light-receiving device according to claim 5, wherein
    the photoelectric conversion layer comprises $In_x Ge_{(1-x)}$ As ($0<x\leq1$), and
    each of the first semiconductor layer and the second semiconductor layer comprises InP.

9. The light-receiving device according to claim 5, further comprising a transparent electrode on an entire surface of the second semiconductor layer.

10. The light-receiving device according to claim 1, wherein
    the first semiconductor layer and the first insulation layer are between the photoelectric conversion layer and the multilayer wiring substrate.

11. The light-receiving device according to claim 1, wherein the first insulation layer comprises at least one of a silicon nitride ($SiN_x$) film or a silicon oxide ($SiO_x$) film.

12. An electronic apparatus, comprising:
    a plurality of pixels, wherein
        each of the plurality of pixels includes a photoelectric conversion layer,
        the photoelectric conversion layer includes a compound semiconductor with a first conductivity-type, and
        the photoelectric conversion layer is configured to absorb a wavelength of an infrared region to generate electric charges;
    a first semiconductor layer on the photoelectric conversion layer;
    a first insulation layer that surrounds each of the photoelectric conversion layer and the first semiconductor layer, wherein
        the first insulation layer has an opening that faces a middle region of the first semiconductor layer,
        the middle region excludes a periphery of the first semiconductor layer facing the photoelectric conversion layer, and
        the middle region of the first semiconductor layer includes a region of a second conductivity-type;
    a contact electrode coupled to the region of the second conductivity-type;

a multilayer wiring substrate on a surface opposite to a light-entering surface of the photoelectric conversion layer, wherein the multilayer wiring substrate includes:
a support substrate;
an inter-insulation layer on the support substrate;
a readout circuit within the inter-insulation layer, wherein the readout circuit includes a pixel circuit and a wiring layer; and
a readout electrode on the pixel circuit;
a second insulation layer that is above the inter-insulation layer and below each of the first insulation layer and the contact electrode; and
a coupling layer coupled to the contact electrode, wherein
the coupling layer is on a face of the second insulating layer,
the coupling layer projects in an X-axis direction on the second insulation layer,
the projection of the coupling layer is beyond side surfaces of the opening,
the coupling layer is configured to readout the electric charges through the contact electrode, and
the readout electrode is coupled with the contact electrode through the coupling layer.

13. The electronic apparatus according to claim 12, wherein the photoelectric conversion layer is separated by the first insulation layer for each of the plurality of pixels.

* * * * *